(12) United States Patent
Sharkey et al.

(10) Patent No.: US 6,923,832 B1
(45) Date of Patent: Aug. 2, 2005

(54) REVISION TIBIAL COMPONENT

(75) Inventors: Peter F. Sharkey, Penn Valley, PA (US); David J. Stumpo, Venetia, PA (US)

(73) Assignee: Trigon Incorporated, McMurray, PA (US)

(*) Notice: Subject to any disclaimer, the term of this patent is extended or adjusted under 35 U.S.C. 154(b) by 189 days.

(21) Appl. No.: 10/102,760

(22) Filed: Mar. 21, 2002

(51) Int. Cl.$^7$ ................................................ A61F 2/38
(52) U.S. Cl. ................................ 623/20.34; 623/20.14
(58) Field of Search .......................... 623/20.34, 20.14, 623/20.15, 20.16, 20.17, 20.18, 20.19, 20.2, 20.21, 20.25, 20.26, 20.27, 20.32, 20.33

(56) References Cited

U.S. PATENT DOCUMENTS

| | | | |
|---|---|---|---|
| 4,340,978 A | 7/1982 | Buechel et al. | 3/1.911 |
| 4,714,474 A | 12/1987 | Brooks, Jr. et al. | 623/20 |
| 4,743,261 A | 5/1988 | Epinette | 623/20 |

(Continued)

FOREIGN PATENT DOCUMENTS

| | | | |
|---|---|---|---|
| WO | WO 00/06058 | 2/2000 | A61F/2/38 |

OTHER PUBLICATIONS

US 5,358,528, 10/1994, Tomier (withdrawn)

*Primary Examiner*—Pedro Philogene
(74) *Attorney, Agent, or Firm*—Kirkpatrick & Lockhart LLP (57) ABSTRACT

A tibial implant is provided having a stem, a tray, a bushing for joining the stem and the tray, and a locking member. In use, the stem of the implant is inserted into the medullary canal of a natural tibia and the tray rests on a resected surface at the proximal end of the tibia. The tray includes a central position and an engagement portion on a lower surface thereof. The bushing includes a proximal axis of alignment in alignment with the central position of the tray and a distal axis of alignment that is co-linear to the longitudinal axis of the stem. The engagement portion of the tray is comprised of a dovetailed ring member. The bushing also includes, on a proximal end thereof, an engagement surface having first and second pairs of surfaces for, respectively, passage through the opening of the ring member and sliding complementary engagement with the dovetailed ring member. The engagement surface of the bushing, when positioned within the ring member of the tray, is freely rotatable within the ring member about the proximal axis. The distal and proximal axes of alignment may be co-linear or spaced from each other a distance up to about 10 mm to allow the center of the tray to be offset from the longitudinal axis of the stem, thereby accommodating a variety of patient anatomies. The locking member locks the bushing in a desired degree of rotation within the ring. A system comprising interchangeable components is also provided.

33 Claims, 8 Drawing Sheets

U.S. PATENT DOCUMENTS

| | | | |
|---|---|---|---|
| 4,865,607 A | 9/1989 | Witzel et al. | 623/20 |
| 4,883,488 A | 11/1989 | Bloebaum et al. | 623/20 |
| 4,923,472 A | 5/1990 | Ugolini | 623/20 |
| 4,938,769 A | 7/1990 | Shaw | 623/20 |
| 5,062,852 A | 11/1991 | Dorr et al. | 623/20 |
| 5,074,880 A | 12/1991 | Mansat | 623/20 |
| 5,190,415 A | 3/1993 | Allerton | 623/20.33 |
| 5,194,066 A * | 3/1993 | Van Zile | 623/20.15 |
| 5,271,737 A | 12/1993 | Baldwin et al. | 623/20 |
| 5,290,313 A | 3/1994 | Heldreth | 623/20 |
| 5,326,359 A | 7/1994 | Oudard | 623/20 |
| 5,344,461 A * | 9/1994 | Phlipot | 623/20.16 |
| 5,405,396 A | 4/1995 | Heldreth et al. | 623/20 |
| 5,613,970 A | 3/1997 | Houston et al. | 606/88 |
| 5,702,463 A | 12/1997 | Pothier et al. | 623/20 |
| 5,782,920 A * | 7/1998 | Colleran | 623/20.34 |
| 6,013,103 A | 1/2000 | Kaufman et al. | 623/20 |
| 6,090,144 A | 7/2000 | Letot et al. | 623/20 |
| 6,126,692 A | 10/2000 | Robie et al. | 623/20 |
| 6,139,581 A | 10/2000 | Engh et al. | 623/20.34 |
| 6,146,424 A | 11/2000 | Gray, Jr. et al. | 623/20.34 |
| 6,149,687 A | 11/2000 | Gray, Jr. et al. | 623/20.34 |
| 6,162,255 A | 12/2000 | Oyola | 623/20.34 |
| 6,168,627 B1 | 1/2001 | Huebner | 623/19.11 |
| 6,355,045 B1 * | 3/2002 | Gundlapalli et al. | 606/88 |
| 6,428,577 B1 * | 8/2002 | Evans et al. | 623/20.29 |
| 6,500,208 B1 * | 12/2002 | Metzger et al. | 623/20.28 |
| 6,506,216 B1 * | 1/2003 | McCue et al. | 623/20.34 |

* cited by examiner

REVISION TIBIAL COMPONENT

BACKGROUND OF THE INVENTION

Knee joint arthroplasty is a common surgical procedure by which a failing natural knee is replaced with a prosthetic knee. The natural knee may fail due to trauma, such as a sports injury or vehicular accident, or due to degenerative disease, such as arthritis.

There are two types of prosthetic knees: a primary knee and a revision knee. Primary knee prostheses are used when failure of the natural knee is not so severe. For example, primary knee prostheses can be used when the ligaments in the natural knee are still intact. Revision knee prostheses are used for more severe failure of the natural knee or failure of a primary knee prosthesis.

In patients who require a revision knee system, there is a lot of bone loss, and therefore, a lack of normal bony reference points, or landmarks, for properly aligning the implant. In these cases, surgeons use the intramedullary canal of the tibia as the landmark for positioning the tibial prosthesis. However, problems arise in positioning the implant because the location of the natural canal varies among individuals. For example, if the tibial stem of the implant is not properly aligned with respect to the intramedullary canal in the medial/lateral direction, the tibial tray will not fit correctly on top of the tibia and will overhang at least one side of the tibia.

Conventional tibial prostheses include a tibial tray with a tibial stem. In many tibial prostheses, the stem is fixed relative to the tibial tray. A few commercially available tibial prostheses include either a nut and bolt or a bushing adjoining the tibial tray and tibial stem. These bushings extend deep into the patient's tibia, requiring a large amount of a patient's natural bone to be removed in order to implant the prosthesis. The removal of large amounts of otherwise healthy bone tissue impedes the healing process and promotes movement of the prosthesis within the knee joint.

BRIEF SUMMARY OF THE INVENTION

The present invention overcomes the aforementioned problems by providing a prosthetic revision tibial component that is used to replace a severely damaged natural knee or an existing tibial component. Revision tibial components are commonly required in patients with severe trauma or degenerative disease of the knee.

The implant of the present invention is configured for positioning, in use, in the natural tibia and comprises a stem, a tray, a bushing for joining the stem and the tray, and a locking member. The implant of the present invention also comprises a bushing for joining a stem and tray.

The stem is configured for insertion, in use, in the intramedullary canal of a tibia and includes a longitudinal axis, a distal end and a proximal end. The tray includes an upper surface, a lower surface and an engagement portion positioned on the lower surface. In one embodiment, the engagement portion defines at least in part, a dovetailed surface.

The invention also includes a bushing that joins the stem and the tray. The bushing includes a proximal end and a distal end. The proximal end of the bushing has a proximal axis of alignment and an engagement surface that is configured for engagement with the engagement portion of the tray. At least a portion of the engagement surface of the bushing is configured for sliding engagement with the dovetailed surface of the engagement portion of the tray, and rotational movement relative to the tray.

In one embodiment, the engagement portion of the tray defines a ring member having an opening. The dovetailed surface is positioned on the inner ring. The engagement surface of the bushing preferably includes a first set of surfaces sized to fit through the opening in the ring and a second set of surfaces configured for complementary sliding engagement with the dovetailed surface of the ring. Preferably, the first set of surfaces includes a pair of opposing surfaces that are parallel to each other, and the second set of surfaces includes a pair of opposing, arced dovetailed surfaces that are generally perpendicular to the first set of surfaces, forming a generally rectangular protrusion, but having opposing arched edges. In an embodiment of the invention comprising a system of interchangeable components, at least two sets of bushings are provided, a first set and a second set. Both sets of bushings are symmetrical about a plane of symmetry. In the first set of bushings, the first set of surfaces is positioned one on each side of the plane of symmetry, and the second set of surfaces is positioned to intersect the plane of symmetry. In a second set of bushings, the second set of surfaces is positioned one on each side of the plane of symmetry, and the first set of surfaces is positioned to intersect the plane of symmetry. In this system, 360 degrees of rotation about the proximal axis while maintaining a secure engagement between the bushing and the tray is achieved. Each of the first and second sets of bushings preferably includes a plurality of bushings within the set that differ from each other in that each one has a different offset distance between said proximal and distal axes within a range from 0 to about 10 mm.

The distal end of the bushing of the present invention has a distal axis of alignment and is configured for engagement with the proximal end of the stem such that the distal axis of alignment of the bushing is substantially co-linear to the longitudinal axis of the stem. The bushing is directly attached to and interposed between the tray and the stem, so that the distance between the proximal and distal ends of the bushing are small relative to the distance between the proximal and distal ends of the stem. In one embodiment, the bushing may be integrally attached to the proximal end of the stem.

The locking member, preferably a set screw, locks the bushing in a desired degree of rotation within the ring on the tray.

The implant of the present invention can be adjusted in both the media/lateral direction and the anterior/posterior direction to accommodate a wide range of patient anatomies. In addition, because of the relative size and position of the bushing, it does not extend deeply into a patient's tibia, thereby avoiding the need to remove excessive amounts of healthy bone to fit bulky components. The implant of the present invention is well suited for use, and typically, but not necessarily is used, in conjunction with prosthetic patellar, condylar and/or femoral components.

Other details, objects and advantages of the present invention will become apparent with the following brief description of the several views of the drawings and the detailed description of the invention.

BRIEF DESCRIPTION OF THE SEVERAL VIEWS OF THE DRAWINGS

For the purpose of illustrating the preferred embodiments of the revision tibial component of the present invention and not for limiting the same, reference is made to the drawings in which.

DETAILED DESCRIPTION OF THE INVENTION

Figure 1:
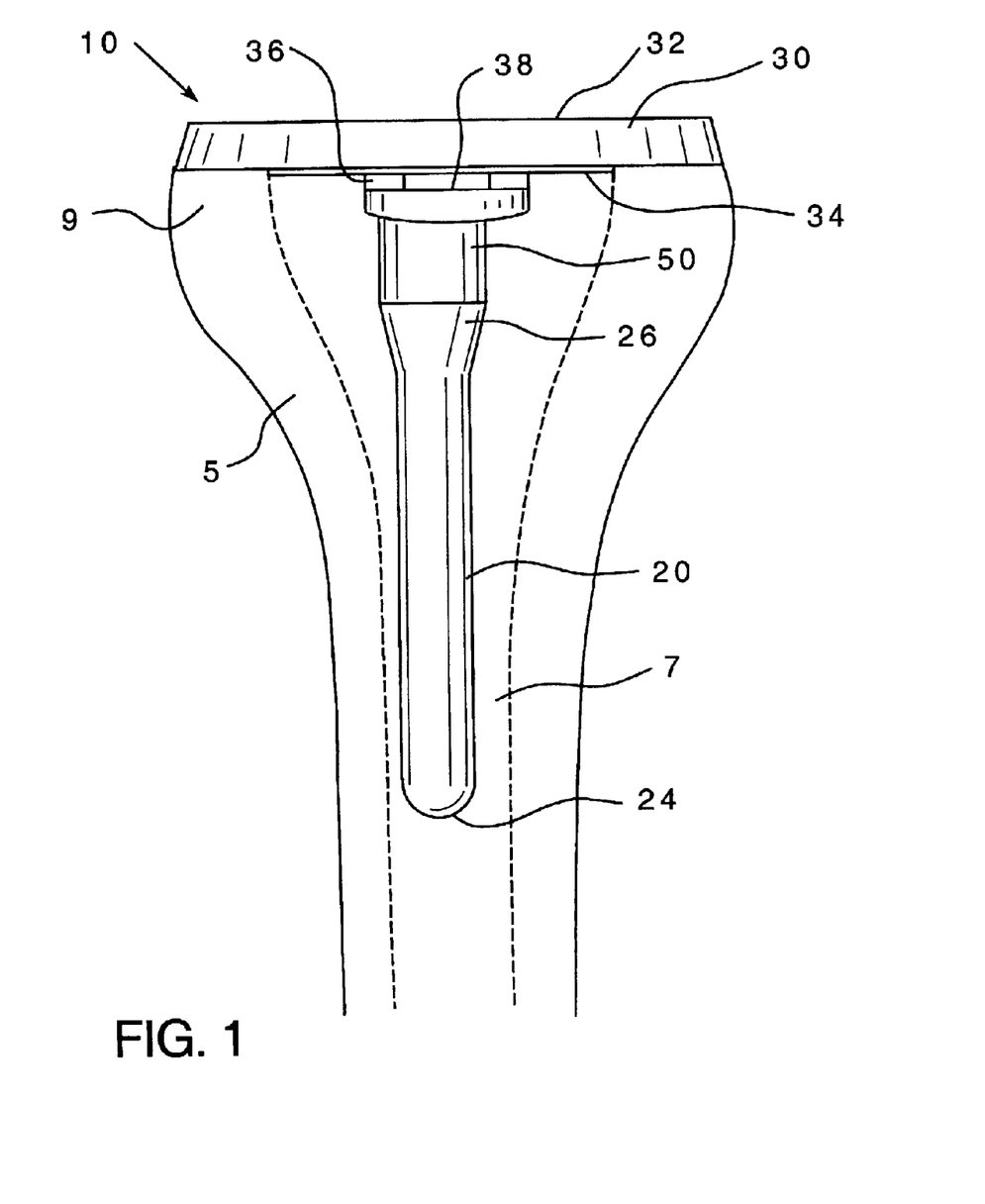
FIG. 1 is an anterior view of an embodiment of a fully assembled revision tibial implant, as it would be implanted into a patient's tibia.

FIGS. 1 through 14 illustrate one embodiment of the revision tibial implant 10 of the present invention. FIG. 1 shows an embodiment of the implant 10, fully assembled, as it would be implanted into a patient's tibia 5. The implant 10 includes a stem 20, a tray 30, a bushing 50 for joining the stem 20 to the tray 30, and a locking member 80 (hidden in FIG. 1). The implant 10 of the present invention is well suited for use, and typically, but not necessarily is used, in conjunction with prosthetic patellar, tibial insert and/or femoral components.

Stem 20 is configured for insertion, in use, in a natural tibia 5. Stem 20 may have any one of a variety of different combinations of length, width and cross-sectional configurations to accommodate different patient anatomies. In one embodiment, the stem 20 is circular in cross-section.

Figure 2:
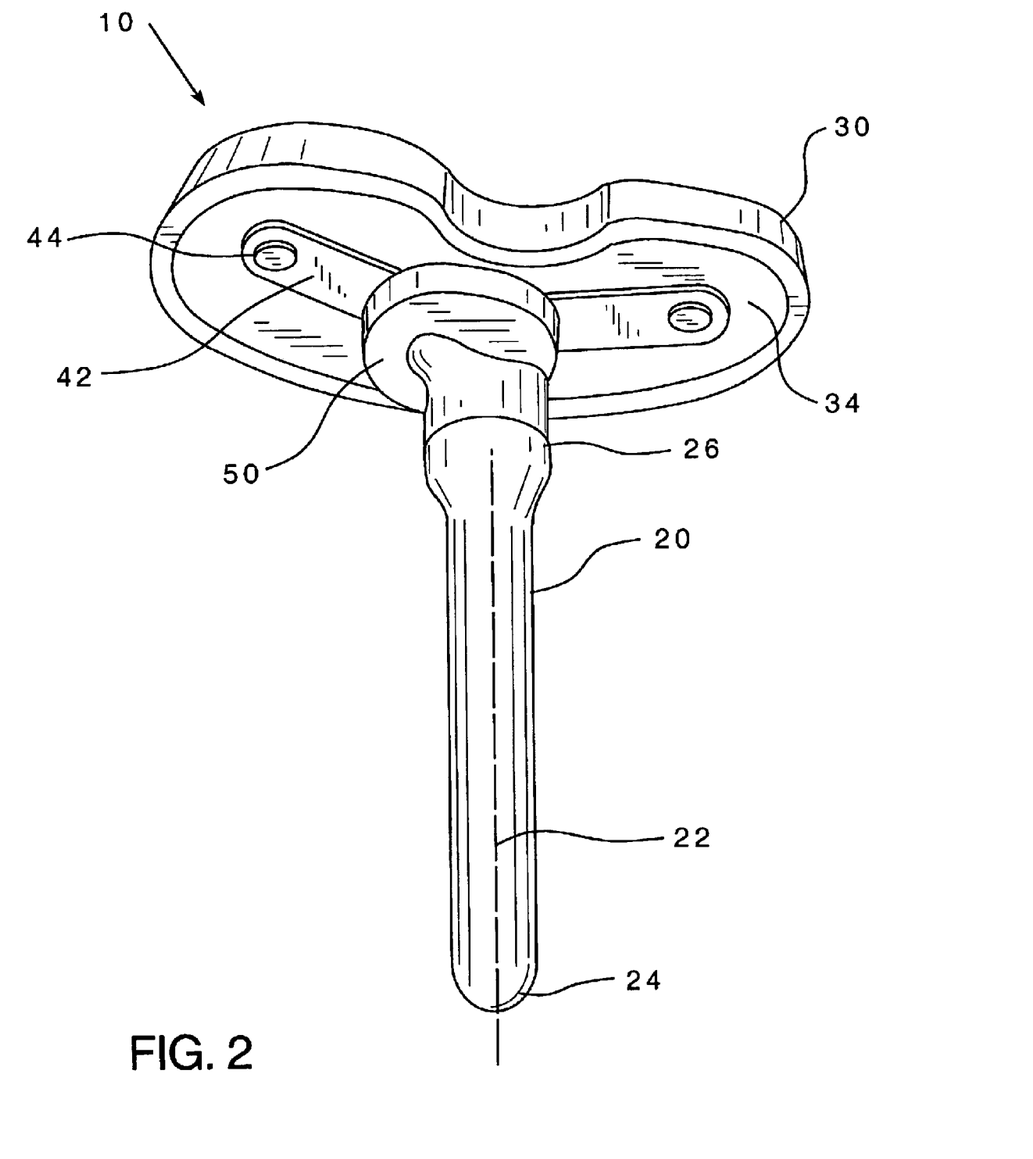
FIG. 2 is an isometric view of the posterior side of the assembled tibial implant of FIG. 1.

Referring to the embodiment shown in FIG. 2, the stem 20 has a longitudinal axis 22, a distal end 24 and a proximal end 26. The distal end 24 of the stem 20 is configured for positioning, in use, in the intramedullary canal 7 of a patient's tibia 5. The proximal end 26 of the stem 20 is configured for engagement with a bushing 50. The engagement surfaces may be threaded, or may include a keyed locking path or any other suitable configuration for securely locking the bushing 50 and the stem 20 together. The longitudinal axis 22 is located through the center of the stem 20. In some embodiments of the stem (not shown), it may be necessary to curve the stem along its length to accommodate patient anatomies. In these embodiments, the longitudinal axis 22 would not be straight, but would follow the curve of the stem 20. The degree of curvature would be dictated by anatomical constraints. In a system comprising interchangeable components for implant, at least one stem 20 is provided. Alternatively, multiple stems 20 are provided. Each stem 20 has a proximal end configured to engage the distal end of any one of a variety of interchangeable bushings 50, but differing in length, cross-sectional dimensions and longitudinal curvature. In another embodiment, the bushing 50 may be integrally engaged with the stem 20.

Figure 4A:
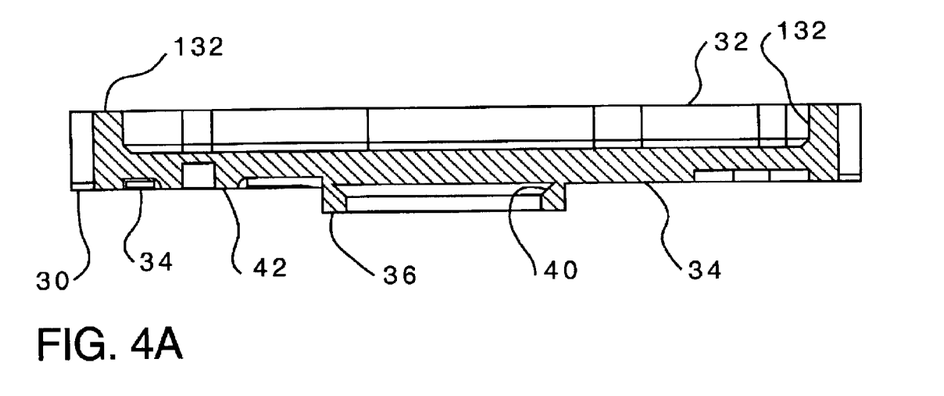
FIGS. 4A & B are section views of embodiments of the tray of FIG. 3 along the line I—I.
Figure 4B:
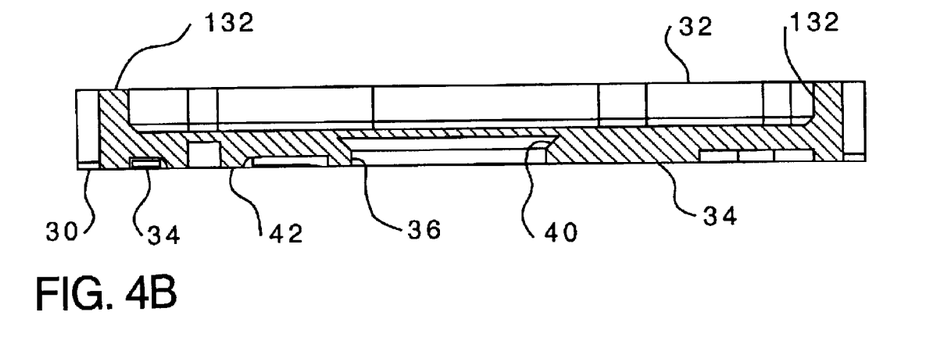
Figure 5:
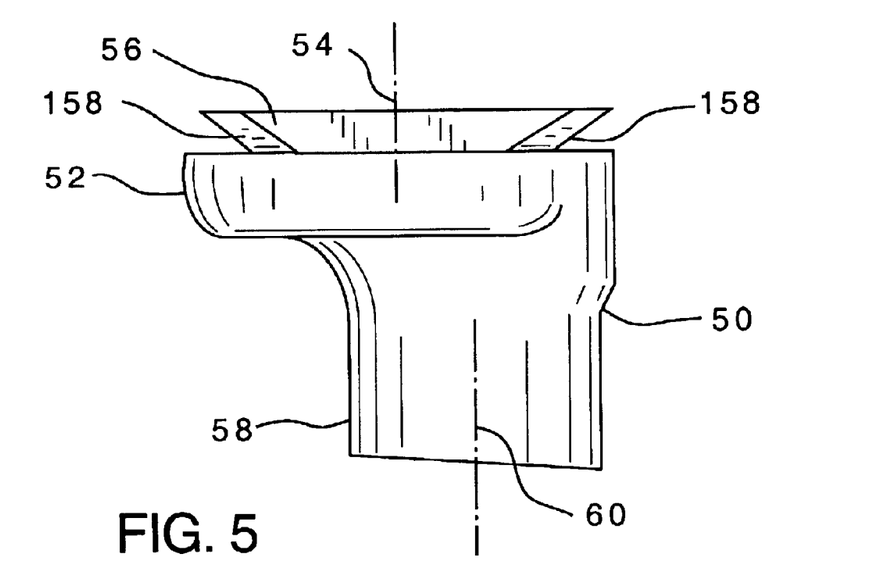
FIG. 5 is a side view of an embodiment of the bushing.
Figure 6:
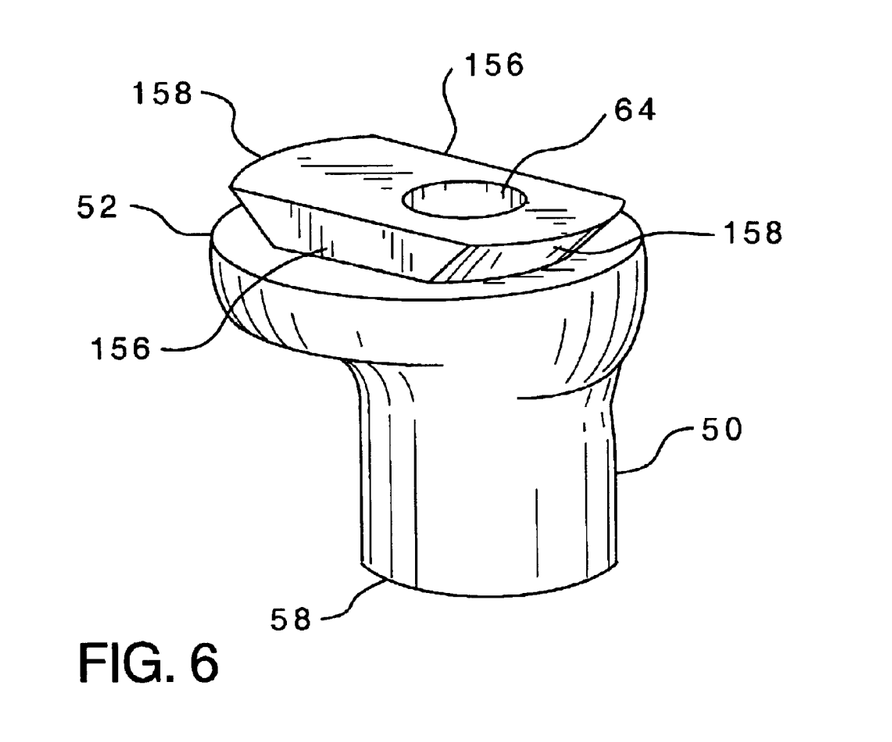
FIG. 6 is an isometric view of the bushing of FIG. 5.

Tray 30 is configured for positioning, in use, on top of a patient's resected tibia, wherein the proximal end 9 of the tibia 5 has been resected to allow for attachment of the implant 10. The configuration of the tray 30 can have a variety of shapes and sizes. In one embodiment, it conforms, along its perimeter, to the perimeter of the resected tibia. The tray 30 may be, but need not be, symmetrical in the medial/lateral direction. Symmetry permits use of the tray in either a right or left leg. Referring to the embodiment shown in FIGS. 4A&B, the tray 30 has an upper surface 32, a lower surface 34, and an engagement portion 36.

The upper surface 32 of the tray 30 may be generally flat, with a flanged lip 132 around the perimeter for receiving and securing in place an insert (not shown) configured for contact, in use, with a natural or prosthetic condyle. Wedge shaped augmentation sections may be inserted between the lower surface 34 of the tray 30 and the resected surface of the tibia, or between the upper surface 32 and a condylar insert.

The lower surface 34 of the tray 30 may also be generally flat. The lower surface 34 includes the engagement portion 36 which may protrude from the surface 34 (FIG. 4A) or define a recess therein (FIG. 4B).

Figure 3:
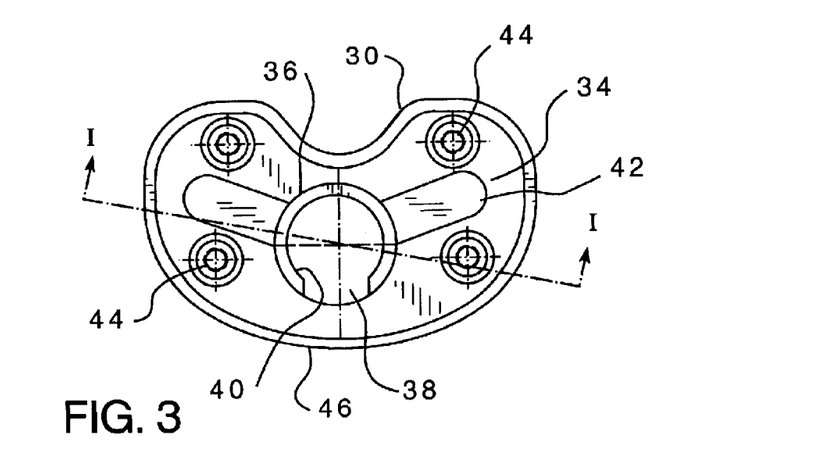
FIG. 3 is a plan view of the lower surface of an embodiment of a tray.

Referring to the embodiments shown in FIGS. 3 and 4A&B, the engagement portion 36 includes a ring having an opening 38 and an inner dovetailed surface 40. The ring can have any one of a variety of diameters and heights, within the limitations of the tray 30 and the anatomical constraints of the patient. In one embodiment, the ring would have a diameter of 22 mm, a height of 2.5 mm and an opening 38 in the ring of about 12 mm. Those skilled in the art will appreciate that, within the constraints of patient anatomies, other dimensions may be used without departing from the scope of the invention. The opening 38 receives a leading edge of the engagement portion of the bushing 50, as described in more detail herein. The opening 38 can be located anywhere along the ring. In FIG. 3, it is shown on the anterior side 46 of the tray 30.

The tray 30 preferably includes struts 42 to increase the strength of the tray 30. The struts provide added strength to absorb high stress and pressure. In one embodiment, the struts 42 are located on the lower surface 34 of the tray 30 for augmentation fixation, if desired by the surgeon. Threaded holes 44 may be positioned within the struts 44 or to either or both sides of the struts 42, as shown in the embodiments of FIGS. 2 and 3, respectively. When augmentation is needed for proper alignment of the implant components relative to the natural or a prosthetic condyle, the surgeon can secure the augmentation sections with a suitable screw through holes 44 to the lower surface 34 of the tray 30. The augmentation sections may be made of cobalt chrome or other biocompatible materials.

The implant 10 includes a bushing 50 for joining the stem 20 to the tray 30. The bushing 50 can be shaped in a variety of configurations. Referring to the embodiments of FIGS. 5–13, the bushing 50 is shown as being symmetrical along an anterior/posterior plane of symmetry 150, so that it can be used in either the right or left knee. However, the bushing does not have to be symmetrical and may be right or left knee specific. In the embodiment shown in FIGS. 4 and 5, the bushing 50 has a proximal end 52 and a distal end 58.

Referring again to FIGS. 5–13, the proximal end 52 is shown with a proximal axis of alignment 54 and an engagement surface 56 for engagement with the engagement portion 36 of the tray 30. The proximal axis of alignment 54 is shown located generally through the center of the proximal end 52 of the bushing 50. The engagement surface 56 is configured for capture and rotational movement relative to and within the ring of the tray 30. The axis of rotation is about the proximal axis of alignment 54. At least a portion of the engagement surface 56 of the bushing 50 is configured for complementary engagement to the dovetailed surface 40 of the engagement portion 36 of the tray 30.

The engagement surface 56 may have a first set of surfaces 156 sized to fit in the opening 38 and a second set of surfaces 158 configured for complementary engagement to the dovetailed surface 40 of the tray 30. The first set of surfaces 156 may be comprised of a pair of opposing surfaces, generally parallel to the anterior/posterior plane of symmetry 150. The second set of surfaces 158 defines a pair of opposing arcuate dovetailed surfaces aligned generally perpendicular to the first set of surfaces 156, intersecting the anterior/posterior plane 150. The orientation of the surfaces can be rotated by 90, with the first set of surfaces 156 intersecting and generally perpendicular to the anterior/posterior plane 150 of the bushing 50 and the second set of surfaces 158 positioned on each side of the plane 150. In a system of the present invention comprising interchangeable components, first and second sets of bushings of each orientation may be provided.

The distal end 58 of the bushing 50 has a distal axis of alignment 60. The distal axis of alignment 60 is located generally through the center of the distal end 58 of the bushing 50, substantially parallel to the proximal axis of alignment 54, along the length of the bushing 50. The distal end 58 of the bushing 50 is configured for engagement with the proximal end 26 of the stem 20 such that the distal axis of alignment 60 of the bushing 50 is co-linear to the longitudinal axis 22 of the stem 20. Those skilled in the art will recognize that when the stem 20 is curved, only the proximal end of the longitudinal axis 22 will be substantially co-linear to the distal axis of alignment 60.

Figure 8:
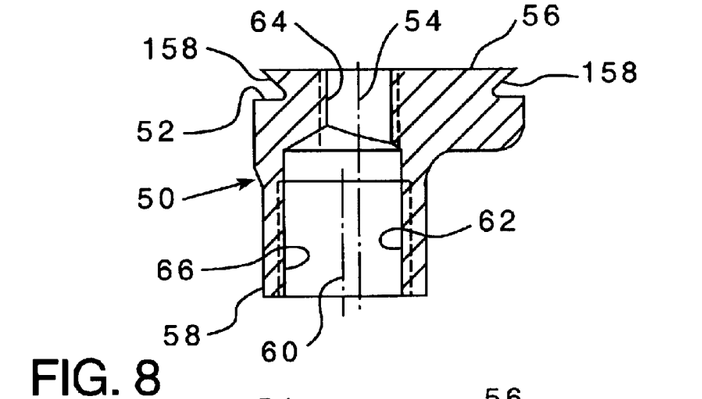
FIG. 8 is a side section view of the bushing of FIG. 5, showing an offset between the proximal and distal axes of alignment of the bushing.
Figure 9:
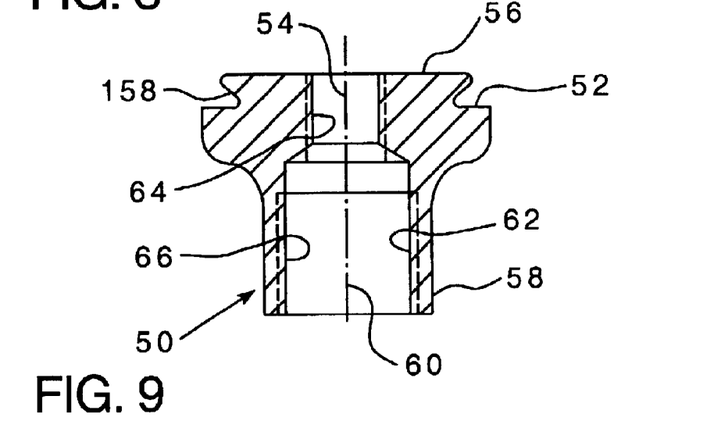
FIG. 9 is a side section view of a bushing, showing a zero offset between the co-linear proximal and distal axes of alignment of the bushing.
Figure 10:
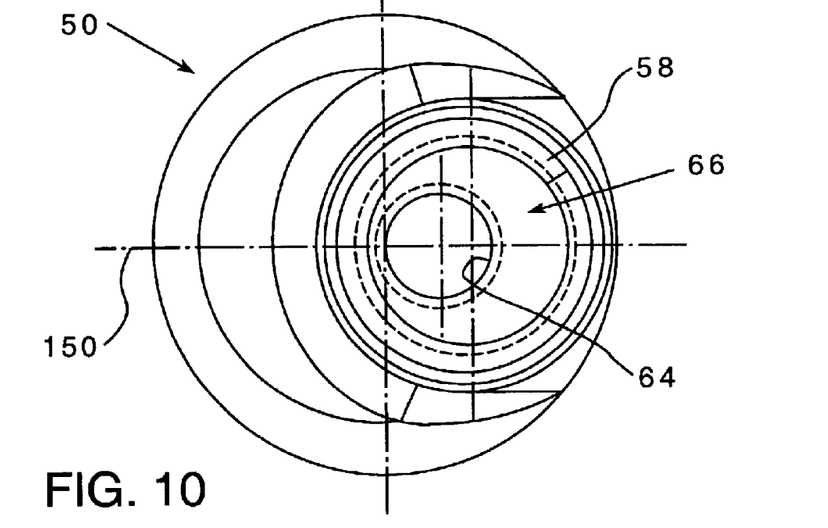
FIG. 10 is a view of the distal end of the bushing of FIG. 7.
Figure 11:
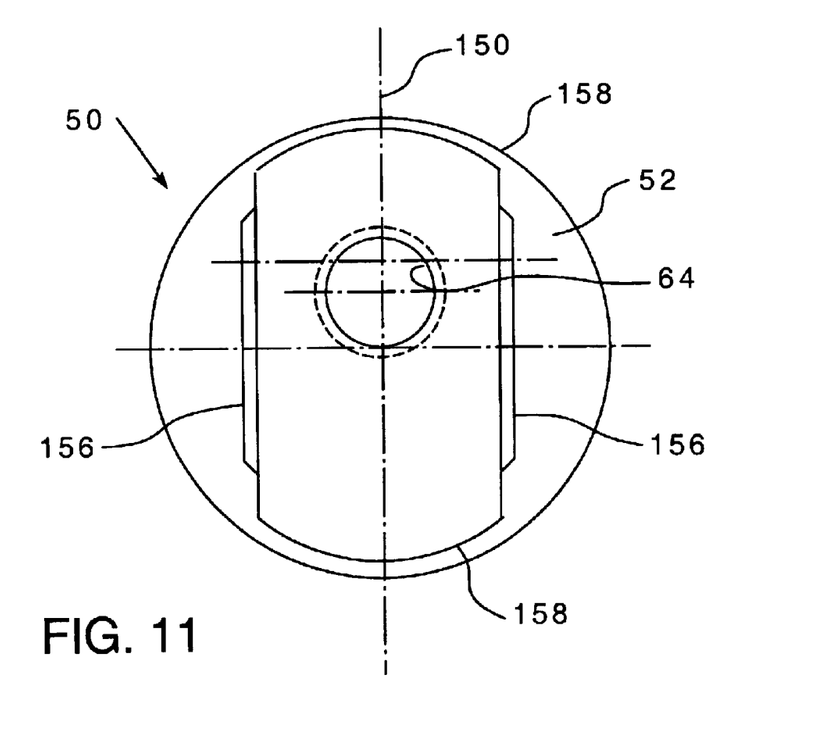
FIG. 11 is a view of the proximal end of the bushing of FIG. 7.
Figure 12:
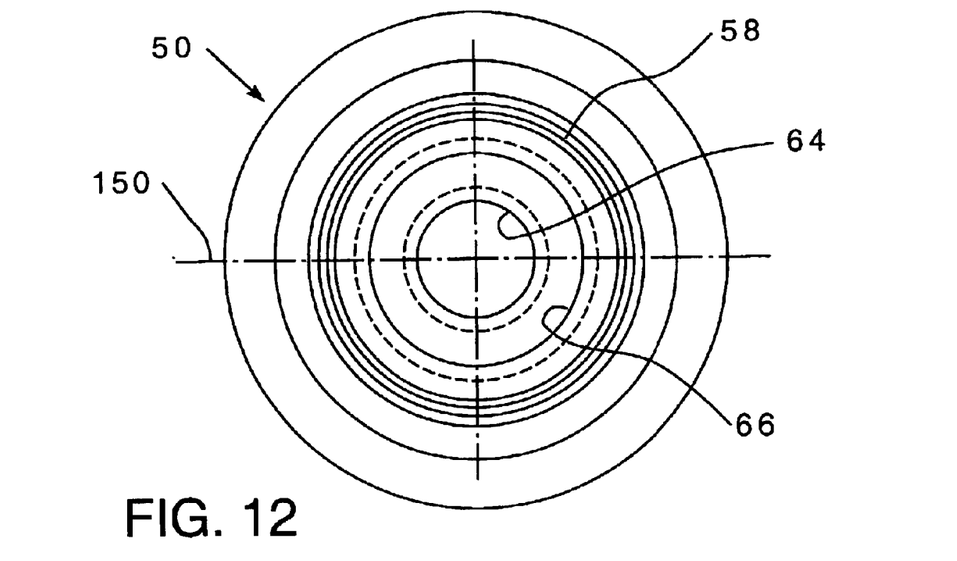
FIG. 12 is a view of the distal end of the bushing of FIG. 9.
Figure 13:
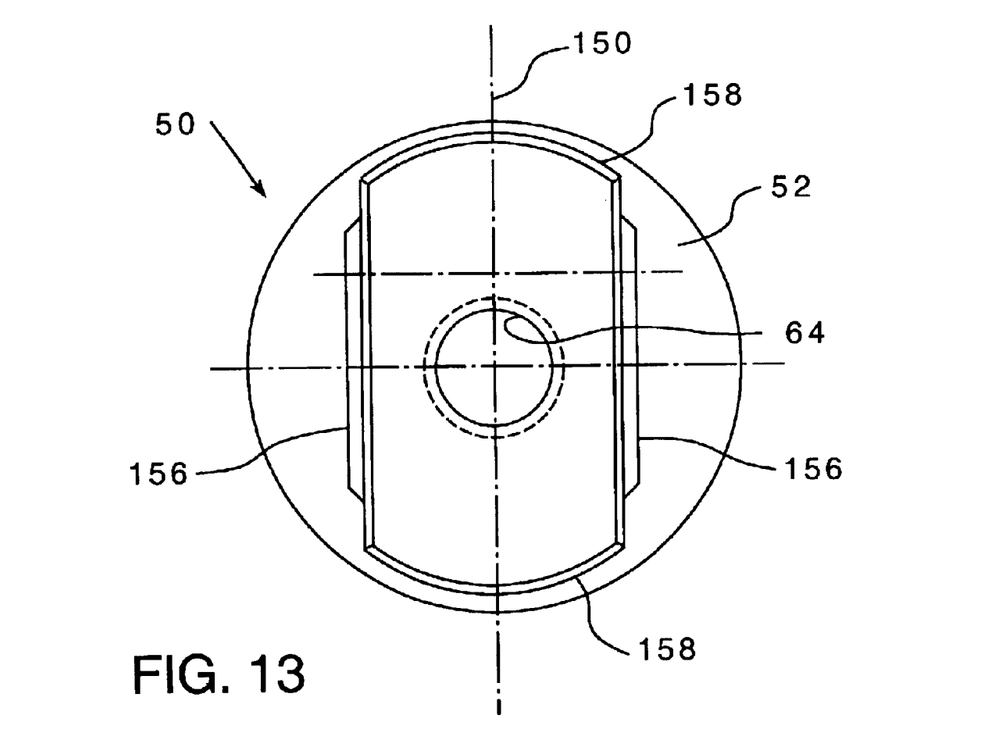
FIG. 13 is a view of the proximal end of the bushing of FIG. 9.

Referring to the embodiment shown in FIG. 9, the distal axis of alignment 60 may be co-linear to the proximal axis of alignment 54 or, as shown in FIG. 8, may be offset a predetermined distance from it. The distance between the proximal and distal axes of alignment 54, 60 determines the amount of offset. As shown in FIG. 9, the axes 54, 60 may be co-linear to each other, defining a zero offset. Alternatively, as shown in FIG. 8, the axes 54, 60 may be spaced from each other, defining a desired offset. In one embodiment, the offset may range from 0 to about 10 mm, and when spaced, the offset is a distance up to about 10 mm. In another embodiment, the amount of offset is in the range of 0 to 6 mm, and in yet another embodiment, the amount of the offset is in the range of 0 to 4 mm. In a system comprising interchangeable components for implant, each of the first and second sets of bushings may include bushings having offsets falling within any one or more of the aforementioned ranges, for example, 0, 2 and 4 mm, up to about 10 mm, may be provided so the surgeon can closely match the alignment of a patient's knee.

Referring to the embodiments of FIGS. 7–13, the bushing 50 has a bore 62 therethrough for receiving a locking member 80. The bore 62 extends from the distal end 58 to the proximal end 52 of the bushing 50. The width of the bore 62 is wide enough to allow a locking member 80 (see FIG. 7) to pass through the bore 62 from the distal end 58 to the proximal end 52 of the bushing 50, even if the bushing 50 is offset. The locking member 80 should fit snugly in the proximal end 52 of the bushing 50. The width of the bore 62 need not be constant, but may be wider at the distal end 58 than at the proximal end 52. The bore 62 may be threaded for receiving the locking member 80.

Referring to the embodiments shown in FIGS. 10–13, the bore 62 of the bushing 50 includes a minor bore 64 in the proximal end 52 of the bushing 50 and a major bore 66 in the distal end 58 of the bushing 50. In this embodiment, the minor bore 64 receives the locking member 80 and major bore 66 receives stem 20. The major bore 66 shown is wider in diameter than the minor bore 64. Both the major and minor bores 66, 64 may be threaded to engage the stem 20 and locking member 80, respectively. Those skilled in the art will recognize that other suitable locking surfaces may be used instead of threaded locking surfaces.

Figure 7:
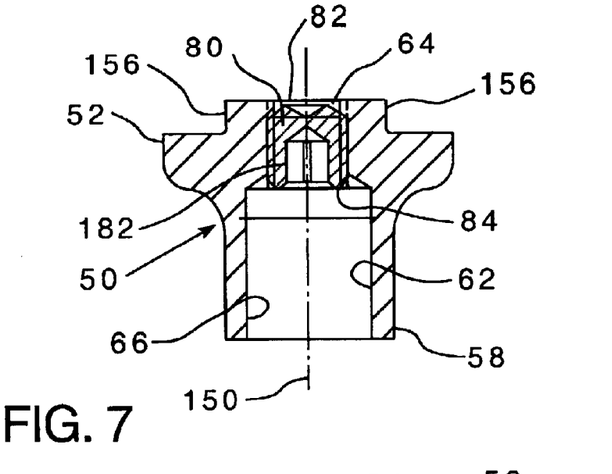
FIG. 7 is a rear section view of the bushing of FIG. 5, with a locking member captured therein.

Locking member 80 locks the bushing 50 at a desired degree of rotation within the ring of the tray 30. The locking member may be any object or device that would lock the position of the bushing 50 on the tray 30. Referring to FIG. 7, the locking member 80 is shown as a set screw that has both a distal end 84 and a proximal end 82. The distal end 84 has a counterbore 182 that allows the set screw to be tightened by means of a tool, such as a torque wrench. The proximal end 82 of the embodiment of the set screw shown has a beveled surface that can extend beyond the proximal end 52 and face of the engagement surface 56 of the bushing 50 so that upon tightening with the tool, it pressed against the lower surface of the tray 30 to pressure fit the bushing to the tray 30. When the bores 64, 66 are threaded, the exterior surface of the locking member 80 will also be threaded to provide a complementary engagement surface. In the implant 10 of the present invention, locking member 80 is captured within the bushing 50, between the tray 30 and the stem 20. Therefore, unlike some prior art implants, the locking member 80 cannot become dislodged after implantation.

Assembly of the implant 10 of the present invention proceeds as follows. A leading edge of engagement surface 56 of the bushing 50 is inserted through the opening 38 of the engagement portion 36 such that the first set of opposing surfaces 156 are positioned to fit through the opening 38. The bushing 50 is advanced into the opening until the leading edge meets the dovetailed surface 40 of the ring, opposite the opening 38. The dovetailed surface 40 of the engagement portion 36 of the tray 30 and the complementary dovetailed second set of surfaces 158 of the engagement surface 56 allow the bushing 50 to rotate smoothly within the ring about the proximal axis of alignment 54. The ability of the bushing 50 to rotate enables the surgeon to match the medial/lateral offset of the implant 10 across a wide range and an almost infinite number of positions, thus enabling a more anatomically aligned fit. In addition, the dovetailed surface 40 of the tray 30 and the complementary dovetailed surface 158 on the bushing 50 allow the bushing 50 to provide excellent medial/lateral stability in use.

Figure 14:
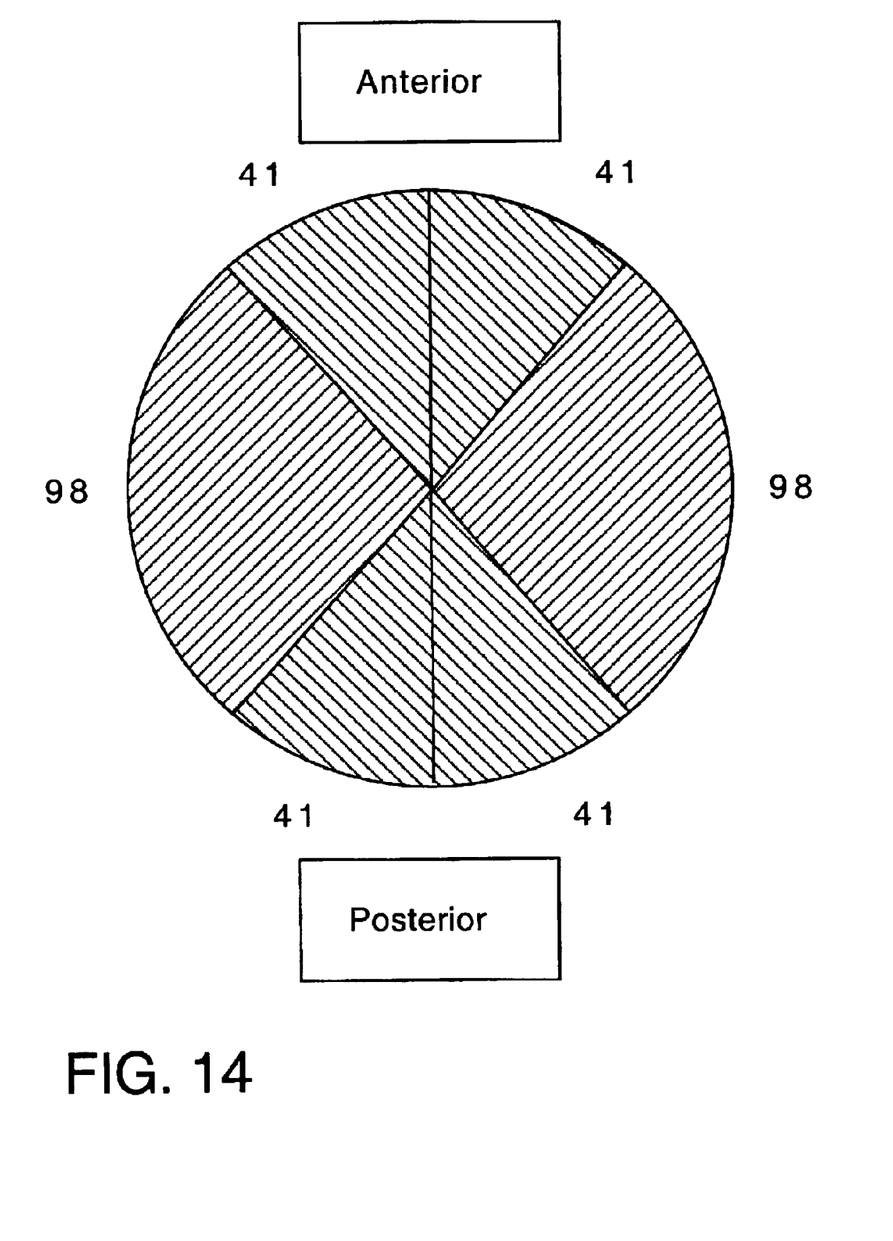
FIG. 14 is a diagram showing the degree of captured rotation for the embodiment of the bushing and tray of FIG. 2.

However, as shown in FIG. 14, the opening 38 creates a zone of reduced stability if the desired position of rotation of the bushing 50 within the ring positions one of the pair of second set of surfaces at the opening 38, such that both second surfaces are not engaged by the dovetailed surface 40 of the ring. In this position, the second set of surfaces fall within the 82 degrees of the ring that defines the opening 38.

Unless tightly secured, the bushing 50 could slide out of the ring on tray 30. The pressure fit of locking member 80 will provide some stability, but not as much as the stability provided when the complementary dovetailed surfaces 40 of the ring and the second set of surfaces 158 are engaged. The bushing 50 must be rotated so that both opposing sides of the second set of surfaces 158 of the engagement surface 56 are held within the dovetail portion of the ring. Referring to the darkly shaded areas of FIG. 14, the more stable position of rotation captures the second set of complementary dovetailed surfaces within the 98 area shown.

The size of the opening 38 determines the limits of maximum rotational stability for the bushing 50. If the size of the opening 38 is smaller, then the size of the lightly shaded area of FIG. 14 decreases and that of the darkly shaded area increases, defining a larger area of rotation through which the bushing 50 can move and still remain engaged on all engagement surfaces with the engagement portion of the tray. Alternatively, if the size of the opening 38 is larger, then the size of the lightly shaded area increases and that of the darkly shaded area decreases, thereby defining a smaller are of rotation though which the bushing 50 can move and still remain fully engaged.

In order to overcome the limits of maximum rotational stability, the implant 10 may have at least two alternative embodiments of the bushing 50. As described herein, in one embodiment, the first set of surfaces 156 may be generally parallel to the anterior/posterior plane 150 and the second set of surfaces 158 are aligned generally perpendicular to the first set of surfaces, intersecting the anterior/posterior plane 150. In another embodiment, the first set of surfaces 156 intersect and are perpendicular to the anterior/posterior plane of the bushing 50 and the second set of surfaces 158 are positioned on each side of the plane 150. In the second embodiment, the diagram shown in FIG. 14 would be rotated 90 degrees. As a result, if proper alignment requires the first embodiment of the bushing 50 to be aligned such that the second set of surfaces 158 are not fully engaged with the dovetail surfaces 40 of the ring, i.e., located in the lightly shaded areas of FIG. 14, then the second embodiment of the bushing 50 of the components in a system for implant could be used. In the second embodiment, the second set of surfaces 158 would be rotated 90 degrees relative to their position on the first embodiment of the bushing 50, such that the second set of surfaces are fully engaged with the dovetailed surfaces on the ring, i.e., in the darkly shaded areas of FIG. 14. Therefore, through the combination of the sets of bushings 50 described above, the implant 10 can achieve both 360 degrees of rotational freedom and maximum stability.

After the surgeon determines the desired medial/lateral position for the bushing 50 for the patient, the bushing 50 is locked on the tray 30 at a desired degree of rotation within the ring by inserting a tool into the counter-bore 182 of locking member 80 and applying sufficient torque to lock the bushing into the desired position on tray 30. A commercial embodiment of the implant 10 would usually be factory assembled so that locking member 80 is pre-positioned in minor bore 64. If the locking member is not pre-positioned, it would be inserted into major bore 66 by the surgeon, so that it travels from the distal end 58 through the major bore 66 to the minor bore 64 at the proximal end 52 of the bushing 50. Once at the proximal end 52 of the bushing 50, the locking member 80 may be tightened so that it extends beyond the face of engagement surface 56 of the bushing 50 and is pressed against the lower surface of tray 30 so as to form a pressure fit against the tray 30, thus securing the bushing 50 to the tray 30.

The implant 10 offers positioning freedom of the stem 20 relative to the tray 30 in both the medial/lateral and anterior/posterior directions. The bushing 50 is configured to allow a desired degree of medial/lateral offset between the axis of the stem 20 and the central position of the tray 30 to accommodate differences in patient anatomy. In addition, the bushing 50, and preferably a set of bushings 50 provided in a system of interchangeable components of the implant 10, can rotate through 360 degrees within the engagement ring of the tray 30 to allow adjustments across the full 360 degrees rather than incrementally. As a result, the implant 10 can accommodate a wide variety of patient anatomies so as to make sure the tray 30 fits properly on the patient's resected tibia while the stem 20 is properly aligned within the intramedullary canal 7 of the tibia 5.

Those skilled in the art will appreciate that the implant 10 and a system comprising interchangeable components of the implant 10 can be made in a variety of sizes that fall within anatomical constraints of the patient population. In order to accommodate patient differences, the various modular components of the implant 10 of the present invention can be made in a variety of sizes, shapes and orientations that are interchangeable with the other components.

The components of the implant 10 of the present invention can be made from any biocompatible material or materials. Suitable materials include cobalt chrome, titanium and stainless steel. The tray 30 and bushing 50 may be made of titanium or cobalt chrome. The stem 20 may be made of titanium. Lastly, the locking member 80 may be made of titanium or cobalt chrome. Although not required, the above materials may be coated with a biocompatible material.

What is claimed is:

1. A tibial implant comprising:
    a stem for insertion, in use, in the intramedullary canal of a natural tibia, said stem having a longitudinal axis, a distal end and a proximal end;
    a tray having an upper surface, a lower surface, and an engagement portion positioned on the lower surface, wherein said engagement portion defines a ring member having a closed upper portion and inner and outer ring surfaces and an opening through said inner and outer ring surfaces, the inner surface of said ring having a dovetailed surface formed thereon;
    a bushing for joining said stem and said tray,
        said bushing having
        a proximal end,
        a proximal axis of alignment,
        an engagement surface on said proximal end for engagement with said engagement portion of said tray,
        at least one portion of said engagement surface configured for insertion through said opening and at least another portion of said engagement surface configured for complementary sliding engagement with said dovetailed surface and rotational movement about said proximal axis of alignment,
        a distal end
        a distal axis of alignment,
        said distal end of said bushing being configured for engagement with said proximal end of said stem, such that said distal axis of alignment of said bushing is substantially co-linear to said longitudinal axis of said stem; and
    a locking member for locking said bushing at a desired degree of rotation about said proximal axis of alignment.

2. The implant of claim 1 wherein said engagement portion is recessed within said lower surface of said tray.

3. The implant of claim 1 wherein said engagement portion protrudes from said lower surface of said tray.

4. The implant of claim 1 wherein said engagement surface includes a first set of surfaces sized to fit through said opening and a second set of surfaces configured for sliding complementary engagement with said dovetailed surface of said ring.

5. The implant of claim 4 wherein said bushing defines a bore therethrough, said bore comprising a minor bore positioned in said proximal end of said bushing, having said proximal axis of alignment passing therethrough, said minor bore being configured for receiving said locking member, said minor bore opening into a major bore positioned in said distal end of said bushing, said major bore having said distal axis of alignment passing therethrough and being configured for receiving said stem, and wherein said bushing is generally symmetrical relative to a plane of symmetry and said first set of surfaces comprises a pair of opposing surfaces positioned generally parallel to each other on opposite sides of the plane of symmetry, and said second set of surfaces comprises a pair of opposing arcuate dovetailed surfaces positioned to intersect the plane of symmetry.

6. The implant of claim 4 wherein said bushing defines a bore therethrough, said bore comprising a minor bore positioned in said proximal end of said bushing, having said proximal axis of alignment passing therethrough, said minor bore being configured for receiving said locking member, said minor bore opening into a major bore positioned in said distal end of said bushing, said major bore having said distal axis of alignment passing therethrough and being configured for receiving said stem, and wherein said bushing is generally symmetrical relative to a plane of symmetry and said second set of surfaces comprises a pair of opposing arcuate dovetailed surfaces positioned on opposite sides of the plane of symmetry, and said first set of surfaces comprises a pair of opposing surfaces positioned generally parallel to each other intersecting the plane of symmetry.

7. The implant of claim 1 wherein said proximal axis of alignment and said distal axis of alignment are co-linear to each other.

8. The implant of claim 1 wherein said proximal axis of alignment and said distal axis of alignment are spaced a distance from each other.

9. The implant of claim 8 wherein said tray has a central position and said proximal axis of alignment lies on a line passing through said central position such that the central position of said tray and said longitudinal axis of the stem, when joined, are offset from each other by the distance between said proximal and distal axes of alignment.

10. The implant of claim 9 wherein the distance of said offset is up to about 10 mm.

11. The implant of claim 9 wherein said offset is within the range of 0 to about 10 mm.

12. The implant of claim 9 wherein said offset is within the range of 0 to about 4 mm.

13. The implant of claim 1 wherein said locking member has a counter-bore therein for receiving a tool for tightening said locking member and a proximal surface that, in use, upon the application of torque, extends beyond said proximal end of said bushing and contacts said tray so as to form a pressure fitting against said tray.

14. The implant recited in claim 5 wherein said minor bore is threaded and said locking member is externally threaded for threaded engagement to each other.

15. The implant recited in claim 5 wherein said major bore is threaded and the proximal end of said stem is threaded for threaded engagement to each other.

16. The implant of claim 1 further comprising a condylar insert secured to the upper surface of said tray.

17. The implant recited in claim 1 wherein said distal end of said bushing is integrally engaged with said proximal end of said stem.

18. A system of interchangeable components comprising:
at least one stem for insertion, in use, in the intramedullary canal of a natural tibia, each said stem having a longitudinal axis, a distal end and a proximal end;
at least one tray, each said tray having an upper surface, a lower surface, a central position and an engagement portion positioned on the lower surface and having, a closed upper portion and, at least in part, a dovetailed surface;
a plurality of bushings, each bushing being structured for joining any one of said at least one stem and tray,
each said bushing having a proximal end, a proximal axis of alignment lying on a line passing through said central position of said tray, and an engagement surface on said proximal end for engagement with said engagement portion of said tray, at least a portion of said engagement surface configured for complementary sliding engagement with said dovetailed surface and rotational movement about said proximal axis of alignment,
each said bushing having a distal end and a distal axis of alignment, said distal end of said bushing being configured for engagement with said proximal end of said stem, such that said distal axis of alignment of said bushing is substantially co-linear to said longitudinal axis of said stem;
said proximal axis of alignment and said distal axis of alignment of each said bushing being positioned a predetermined distance from each other such that the central position of said tray and the longitudinal axis of the stem, when joined, are offset from each other by said distance; and
at least one locking member for locking one said bushing at a desired degree of rotation about said proximal axis of alignment;
wherein each said bushing defines a bore therethrough, said bore comprising a minor bore positioned in said proximal end of said bushing, said minor bore being in axial alignment with said proximal axis of alignment, said minor bore being configured for receiving said locking member, said minor bore opening into a major bore positioned in said distal end of said bushing, said major bore being in axial alignment with said distal axis of alignment, said major bore being configured for receiving said stem.

19. The system of claim 18 wherein each of said plurality of bushings has a different offset distance between said proximal and distal axes within a range from 0 to about 10 mm.

20. The system of claim 18 wherein each of said plurality of bushings has a different offset distance between said proximal and distal axes within a range from 0 to about 6 mm.

21. The system of claim 18 wherein each of said plurality of bushings has a different offset distance between said proximal and distal axes within a range from 0 to about 4 mm.

22. The system of claim 18 wherein each of said plurality of bushings has a different offset distance between said proximal and distal axes of 0 mm, about 2 mm and about 4 mm.

23. The system of claim 17 wherein said engagement portion of said at least one tray is comprised of a ring member having a closed upper portion and inner and outer ring surfaces and an opening through said inner and outer ring surfaces, said dovetailed surface being positioned on the inner surface of said ring.

24. The system of claim 23 wherein said engagement surface of each said bushing includes a first set of surfaces sized to fit through said opening and a second set of surfaces configured for sliding complementary engagement with said dovetailed surface of said ring.

25. The system of claim 24 wherein each said bushing is generally symmetrical relative to a plane of symmetry and said first set of surfaces of each said bushing comprises a pair of opposing surfaces positioned generally parallel to each and said second set of surfaces of each said bushing comprises a pair of opposing arcuate dovetailed surfaces.

26. The system of claim 25 wherein there are at least two sets of bushings, a first set of bushings having said first set of surfaces positioned on opposite sides of the plane of symmetry and said second set of surfaces intersecting the plane of symmetry, and a second set of bushings having said second set of surfaces positioned on opposite sides of the plane of symmetry and said first set of surfaces intersecting the plane of symmetry.

27. The system of claim 26 wherein each of said first and second sets of bushings includes bushings within the set, each having a different offset distance between said proximal and distal axes within a range from 0 to about 10 mm.

28. A tibial implant comprising:
a stem for insertion, in use, in the intramedullary canal of a natural tibia, said stem having a longitudinal axis, a distal end and a proximal end;
a tray having an upper surface, a lower surface, and an engagement member on the lower surface, said lower surface of said tray defining a closed upper surface of said engagement member, said engagement member having side walls with a gap therein forming an opening through said side walls, the inner surface of said side walls forming a ring segment and having a dovetailed surface formed thereon;
a bushing for joining said stem and said tray,
said bushing having
a proximal end,
a proximal axis of alignment,
an engagement surface on said proximal end, said engagement surface configured for insertion through said gap of said engagement member of said tray,
at least a portion of said engagement surface configured for complementary sliding engagement with said dovetailed surface and rotational movement about said proximal axis of alignment,
a distal end
a distal axis of alignment,
said distal end of said bushing being configured for engagement with said proximal end of said stem, such that said distal axis of alignment of said bushing is substantially co-linear to said longitudinal axis of said stem; and
a locking member for locking said bushing at a desired degree of rotation about said proximal axis of alignment;
wherein said bushing defines a bore therethrough, said bore comprising a minor bore positioned in said proximal end of said bushing, having said proximal axis of alignment passing therethrough, said minor bore being configured for receiving said locking member, said minor bore opening into a major bore positioned in said distal end of said bushing, said major bore having said distal axis of alignment passing therethrough and being configured for receiving said stem.

29. The implant of claim 28 wherein said proximal axis of alignment and said distal axis of alignment are co-linear to each other.

30. The implant of claim 28 wherein said proximal axis of alignment and said distal axis of alignment are spaced a distance from each other.

31. The implant of claim 30 wherein said tray has a central position and said proximal axis of alignment lies on a line passing through said central position such that the central position of said tray and said longitudinal axis of the stem, when joined, are offset from each other by the distance between said proximal and distal axes of alignment.

32. The implant of claim 31 wherein said offset is within the range of 0 to about 10 mm.

33. The implant of claim 28 wherein said locking member has a counter-bore therein for receiving a tool for tightening said locking member and has a proximal surface that, in use, upon the application of torque, extends beyond said proximal end of said bushing and contacts said tray so as to form a pressure fitting against said tray.

* * * * *

UNITED STATES PATENT AND TRADEMARK OFFICE
CERTIFICATE OF CORRECTION

| | |
|---|---|
| PATENT NO. | : 6,923,832 B1 |
| APPLICATION NO. | : 10/102760 |
| DATED | : August 2, 2005 |
| INVENTOR(S) | : Sharkey et al. |

It is certified that error appears in the above-identified patent and that said Letters Patent is hereby corrected as shown below:

Title Page
Item (56) US Patent Documents,
Page 2, Column 1, delete "5,190, 415 A, 3/93 Allerton 623/20.33," and substitute therefor --6,190,415, 2/01 Cooke et al, 623/20.33--.

Signed and Sealed this

Twenty-eighth Day of November, 2006

JON W. DUDAS
*Director of the United States Patent and Trademark Office*